(12) United States Patent
Yoshioka et al.

(10) Patent No.: US 11,135,417 B2
(45) Date of Patent: Oct. 5, 2021

(54) MEDICAL VALVE

(71) Applicant: NIPRO CORPORATION, Osaka (JP)

(72) Inventors: Kiyotaka Yoshioka, Osaka (JP);
Hiroyuki Nakagami, Osaka (JP);
Shingo Sakamoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 510 days.

(21) Appl. No.: 15/300,551

(22) PCT Filed: Apr. 7, 2015

(86) PCT No.: PCT/JP2015/060813
§ 371 (c)(1),
(2) Date: Sep. 29, 2016

(87) PCT Pub. No.: WO2015/156272
PCT Pub. Date: Oct. 15, 2015

(65) Prior Publication Data
US 2017/0106182 A1    Apr. 20, 2017

(30) Foreign Application Priority Data
Apr. 8, 2014   (JP) .............................. JP2014-079130

(51) Int. Cl.
*A61M 39/26* (2006.01)
*A61M 5/14* (2006.01)
(Continued)

(52) U.S. Cl.
CPC .............. *A61M 39/26* (2013.01); *A61M 5/14* (2013.01); *A61M 39/04* (2013.01); *A61M 2039/0072* (2013.01); *A61M 2039/1072* (2013.01)

(58) Field of Classification Search
CPC .... A61M 39/045; A61M 39/26; A61M 39/04; A61M 2039/0072; A61M 2039/1072; A61M 5/14
See application file for complete search history.

(56) References Cited

U.S. PATENT DOCUMENTS 5,080,654 A   1/1992  Picha et al.
5,961,497 A * 10/1999  Larkin ................ A61M 39/045
                                                      604/201
(Continued)

FOREIGN PATENT DOCUMENTS

JP    H02-502976 A    9/1990
JP    2004-237133 A   8/2004
(Continued)

OTHER PUBLICATIONS

Oct. 12, 2016 International Preliminary Report on Patentability issued in International Patent Application No. PCT/JP2015/060813.
(Continued)

*Primary Examiner* — Brandy S Lee
*Assistant Examiner* — Hong-Van N Trinh
(74) *Attorney, Agent, or Firm* — Oliff PLC

(57) ABSTRACT

A medical valve which is able to more reliably support an outer peripheral part of an elastic valve body with respect to a housing, and prevent a problem of the elastic valve body becoming dislodged inward. A medical valve includes an elastic valve body with annular grooves formed thereon and a tubular support part formed at an outer peripheral side of an annular joining part positioned between the annular grooves. Inside and outside holding parts engage the annular grooves provided to the valve inside and outside surfaces of the annular joining part. The outside holding part and inside holding part are provided to an opening member, and with the tubular support part, a part projecting inward in an axial
(Continued)

direction is sandwiched and supported between the inside holding part and outside holding part.

18 Claims, 7 Drawing Sheets

(51) Int. Cl.
  *A61M 39/04* (2006.01)
  *A61M 39/00* (2006.01)
  *A61M 39/10* (2006.01)

(56) References Cited

U.S. PATENT DOCUMENTS

| | | |
|---|---|---|
| 2002/0002351 A1 | 1/2002 | Cote et al. |
| 2006/0184140 A1 | 8/2006 | Okiyama |
| 2011/0233435 A1 | 9/2011 | Matsumoto et al. |
| 2015/0294880 A1* | 10/2015 | Anderson ......... H01L 21/31116 438/719 |
| 2016/0015958 A1 | 1/2016 | Ueda et al. |

FOREIGN PATENT DOCUMENTS

| | | |
|---|---|---|
| JP | 2009-172099 A | 8/2009 |
| JP | 2018-202254 A | 12/2018 |
| WO | 89/06553 A2 | 7/1989 |
| WO | 95/15193 A1 | 6/1995 |
| WO | 2012/133131 A1 | 10/2012 |
| WO | WO-2012133131 A1 * 10/2012 | .......... A61M 39/045 |
| WO | 2013/146740 A1 | 10/2013 |
| WO | 2014/162347 A1 | 10/2014 |

OTHER PUBLICATIONS

Dec. 7, 2017 Extended Search Report issued in European Patent Application No. 15776000.0.
Sep. 11, 2017 Search Report issued in European Patent Application No. 15 776 000.0.
Jul. 7, 2015 Search Report issued in International Patent Application No. PCT/JP2015/060813.
Aug. 10, 2018 Office Action issued in Japanese Patent Application No. 2016-512737.
Mar. 6, 2020 Office Action issued in Japanese Patent Application No. 2018-190545.
Aug. 30, 2019 Office Action issued in Japanese Patent Application No. 2018-190545.
Jan. 7, 2021 Office Action issued in Indian Patent Application No. 201627038063.
Jun. 29, 2021 Office Action issued in Japanese Patent Application No. 2020-098763.

* cited by examiner

MEDICAL VALVE

TECHNICAL FIELD

The present invention relates to a medical valve used for a fluid flow path in the medical field such as for a transfusion route or the like, and is capable of connecting a medical connecting tool (male connector) such as a syringe or the like to the fluid flow path.

BACKGROUND ART

With fluid flow paths for performing transfusion, blood collection or the like, a medical valve is used as necessary for making it possible to connect a male connector such as a syringe. For example, with a three-way stopcock or Y-shaped connector which are types of fluid flow path forming members, the fluid flow path is formed between a pair of flow path opening parts, and the medical valve is mounted at the other remaining flow path opening part. Then, by making it possible to connect a male connector such as a syringe or the like to the fluid flow path via this medical valve, it is possible to perform mixed injection of drug solutions or the like.

As one type of medical valve of this kind of medical connector or the like, a split septum type medical valve noted in Japanese Domestic Publication of International Patent Application No. JP-A-H02-502976 (Patent Document 1) and Japanese Unexamined Patent Publication No. JP-A-2004-237133 (Patent Document 2) is known. This medical valve has a structure with a disk-shaped elastic valve body having a slit formed at the center part mounted on an opening member of the housing constituting the opening part of the fluid flow path. Then, by directly inserting the tip of the male connector into the slit of the elastic valve body, it is possible to connect the male connector to the fluid flow path in a communicating state. Also, by extracting the tip of the male connector such as the syringe or the like connected this way from the elastic valve body, with the recovery action of the elastic valve body simultaneous with extracting, the cutoff state of the fluid flow path is maintained.

Also, with the split septum type medical valve, so as not to have separation of the elastic valve body occur when attaching and detaching the male connector, it is necessary to firmly fix the elastic valve body to the opening of the opening member. In light of that, in the past, as shown in both Patent Documents 1 and 2, a structure is used whereby the outer periphery part of the elastic valve body is sandwiched and supported from both sides in the thickness direction by a pair of claw-shaped annular locking projections provided on the opening member.

However, the background art constitution, by which the outer periphery part of the disk-shaped elastic valve body is sandwiched and supported by the pair of claw-shaped annular locking projections, was still insufficient to prevent the problem of the outer periphery part of the elastic valve body separating and falling out from the annular locking projection.

BACKGROUND ART DOCUMENT

Patent Document

Patent Document 1: JP-A-H02-502976
Patent Document 2: JP-A-2004-237133

SUMMARY OF THE INVENTION

Problem the Invention Attempts to Solve

The present invention has been developed in view of the above-described matters as the background, and it is an object of the present invention to provide a medical valve with a novel structure which is able to reliably support the outer periphery part of the disk-shaped elastic valve body on the housing, and to prevent the problem of the elastic valve body falling out inward.

Means for Solving the Problem

A first mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes a slim part that is provided at an outer peripheral side of the center part and is thinner than the center part, and a tubular support part that is formed further to the outer peripheral side than the slim part and projects inward in an axial direction; the opening member includes a tube-shaped outside holding part overlapping an outer peripheral surface of the tubular support part and a tube-shaped inside holding part overlapping an inner peripheral surface of the tubular support part so that the slim part of the elastic valve body is sandwiched and supported between the inside holding part and the outside holding part in the axial direction; the tubular support part is sandwiched and supported at a part projecting inward in the axial direction between the inside holding part and the outside holding part; and the tubular support part has, at the part projecting inward in the axial direction, an axial direction dimension larger than a radius of the center part of the elastic valve body.

With the medical valve constituted according to this mode, with the tubular support part of the elastic valve body, by having the projection height inward in the axial direction be larger, it is possible to increase the area that is supported by the opening member, and possible to ensure a large bearing capacity of the elastic valve body by the opening member.

Also, since the male connector is inserted inward in the axial direction of the medical valve, when inserting the male connector, push-in force is applied inward in the axial direction on the elastic valve body. Along with this push-in force, a tensile force, which is the opposite direction to the push-in force, is applied outward in the axial direction on the tubular support part at the part projecting inward in the axial direction. Therefore, with the tubular support part, by making the projection height inward in the axial direction large, the friction between the opening member and the elastic valve body increases, and combined with the hooking operation of the inside engaging part, makes it possible to reduce the risk of the elastic valve body falling out inward in the axial direction. In particular, by the tubular support part having the axial direction dimension of the part that projects inward in the axial direction greater than the radius of the center part of the elastic valve body as with this mode, it is possible to ensure that the cubic volume of the tubular support part is sufficiently larger than the space (slim part) between the axial directions of the outside holding part and the inside holding part at the inner peripheral side from the tubular support part. This makes it possible to even further reduce the risk of the tubular support part falling out inward in the axial direction passing through between the outside holding part and the inside holding part in the axial direction.

In fact, with the tubular support part of the elastic valve body, by making the projection height large inward in the axial direction which is opposite to the opening direction of the opening member, it is possible to increase the bearing capacity by the opening member, thereby keeping the projection height small in the opening direction of the tubular support part and the opening member. Therefore, it is possible to avoid deterioration in insertion and removal operability of the male connector or larger overall size of the medical valve which easily become problems along with an increase in projection height to outside the opening member at the periphery of the elastic valve body.

A second mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes a slim part that is provided at an outer peripheral side of the center part and is thinner than the center part, and a tubular support part that is formed further to the outer peripheral side than the slim part and projects inward in an axial direction; the opening member includes a tube-shaped outside holding part overlapping an outer peripheral surface of the tubular support part and a tube-shaped inside holding part overlapping an inner peripheral surface of the tubular support part so that the slim part of the elastic valve body is sandwiched and supported between the inside holding part and the outside holding part in the axial direction; the tubular support part is sandwiched and supported at a part projecting inward in the axial direction between the inside holding part and the outside holding part; and the tubular support part includes a radial direction projecting part integrally formed at a tip side of the part projecting inward in the axial direction and extending in a radial direction, and the radial direction projecting part is engaged with the opening member.

With the medical valve constituted according to this mode, by an engaging action on the opening member by the radial direction projecting part provided to the tubular support part at the tip side of the part projecting inward in the axial direction, the elastic valve body can be mounted on the opening member with an even greater slip-out resistance force.

A third mode of the present invention provides the medical valve according to the second mode, wherein the radial direction projecting part extends outward in the radial direction from the tubular support part, and the slim part and the radial direction projecting part of the elastic valve body are compressed in the axial direction in an attached state to the opening member.

With the medical valve constituted according to this mode, since the slim part and the radial direction projecting part of the elastic valve body are both supported on the opening member in a compressed state, there is always a fixing force operating with the elastic reaction force of each part, increasing the bearing capacity of the elastic valve body in relation to the opening member.

A fourth mode of the present invention provides the medical valve according to the second or third mode, wherein a locking projection projecting outward in the axial direction is formed on the radial direction projecting part, and the locking projection is locked to the opening member.

With the medical valve constituted according to this mode, by further forming a locking projection on the radial direction projecting part provided on the tip side of the tubular support part of the elastic valve body, based on the locking action on the locking projection, it is possible to further increase the retaining direction bearing capacity of the tubular support part by the opening member.

A fifth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes a slim part that is provided at an outer peripheral side of the center part and is thinner than the center part, and a tubular support part that is formed further to the outer peripheral side than the slim part and projects inward in an axial direction; the opening member includes a tube-shaped outside holding part overlapping an outer peripheral surface of the tubular support part and a tube-shaped inside holding part overlapping an inner peripheral surface of the tubular support part so that the slim part of the elastic valve body is sandwiched and supported between the inside holding part and the outside holding part in the axial direction; the tubular support part is sandwiched and supported at a part projecting inward in the axial direction between the inside holding part and the outside holding part; and the tubular support part includes a thin part and a thick part provided in the part projecting inward in the axial direction, and the thick part is positioned further inward in the axial direction than the thin part.

With the medical valve constituted according to this mode, by providing the thin part on the tubular support part, the bearing capacity by the inside holding part and the outside holding part that sandwich and support the tubular support part from both inside and outside can operate even more effectively as a retaining resistance force in relation to the thick part positioned further inward in the axial direction than the thin part. As a result, it is possible to further improve the falling-out prevention effect of the elastic valve body. With the tubular support part in relation to the inside holding part and outside holding part overlapping its inner and outer peripheral surfaces, it is not necessary that the changes in the axial direction in the respective thickness dimensions have a corresponding relationship.

A sixth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes a slim part that is provided at an outer peripheral side of the center part and is thinner than the center part, and a tubular support part that is formed further to the outer peripheral side than the slim part and projects inward in an axial direction; the opening member includes a tube-shaped outside holding part overlapping an outer peripheral surface of the tubular support part and a tube-shaped inside holding part overlapping an inner peripheral surface of the tubular support part so that the slim part of the elastic valve body is sandwiched and supported between the inside holding part and the outside holding part in the axial direction; the tubular support part is sandwiched and supported at a part projecting inward in the axial direction between the inside holding part and the outside holding part; and the inside holding part is configured to be pressed to a side of the tubular support part on an outer periphery thereof by the elastic valve body that elastically deforms in accordance with insertion of the male connector into the slit.

With the medical valve constituted according to this mode, with the tubular support part of the elastic valve body, the part projecting inward in the axial direction is sandwiched and supported between the inside holding part and the outside holding part of the opening member. In light of that, when the male connector is inserted in the elastic valve body, the elastically deformed elastic valve body abuts the inside holding part, and the inner peripheral surface of the inside holding part is pressed toward the outer periphery. As a result, the bearing capacity in relation to the tubular support part between the inside holding part and the outside holding part can be increased, and falling out of the elastic valve body inward in the axial direction can be inhibited.

With this mode, for example, it is preferable for the tubular support part to have the axial direction dimension of the part projecting inward in the axial direction larger than the radius of the center part of the elastic valve body. By so doing, the center part of the elastically deformed elastic valve body can apply pressing force on the inside holding part across the entire surface, and it is possible to have the tubular support part sandwiched with even more stability between the inside holding part and the outside holding part.

A seventh mode of the present invention provides the medical valve according to the sixth mode, wherein a rigidity of the inside holding part is smaller than rigidities of the outside holding part and the male connector.

With the medical valve constituted according to this mode, with the tubular support part of the elastic valve body supported between the inside holding part and the outside holding part, based on the inner peripheral surface of the inside holding part being pressed by the elastic valve body by the male connector being inserted, the effect of improving the holding force on the tubular support part is more effectively achieved.

An eighth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes a slim part that is provided at an outer peripheral side of the center part and is thinner than the center part, and a tubular support part that is formed further to the outer peripheral side than the slim part and projects inward in an axial direction; the opening member includes a tube-shaped outside holding part overlapping an outer peripheral surface of the tubular support part and a tube-shaped inside holding part overlapping an inner peripheral surface of the tubular support part so that the slim part of the elastic valve body is sandwiched and supported between the inside holding part and the outside holding part in the axial direction; and the tubular support part is held in a compressed state at a part projecting inward in the axial direction between the inside holding part and the outside holding part.

With the medical valve constituted according to this mode, since the tubular support part is fixed in a compressed state at the part projecting inward in the axial direction between the inside holding part and the outside holding part, a repellent force is always applied from the tubular support part in relation to the inside holding part and the outside holding part. By so doing, it is possible to increase the friction between the tubular support part and the inside holding part as well as between the tubular support part and the outside holding part, and falling out of the tubular support part is even more effectively prevented. This makes it possible to further increase the falling-out prevention effect for the elastic valve body.

With this mode, it is possible to suitably use a mode for which the opening member main body includes a supporting wall for supporting the tubular support part at the radial direction outside end part of the tip of the part projecting inward in the axial direction, and a projecting part for welding that projects onto the overlapping surfaces in the axial direction of the supporting wall and the outside holding part is formed, and by the projecting part for welding being ultrasonically welded, the outside holding part is fixed to the supporting wall.

With this medical valve, the projecting part for welding is formed projecting onto the overlapping surfaces in the axial direction of the supporting wall and the outside holding part provided on the opening member main body, and since the opening member main body and the outside holding part are ultrasonically welded at the projecting part for welding, it is possible to efficiently and reliably perform this ultrasonic welding. Furthermore, since the outside holding part is fixed to the supporting wall which is positioned on the outer peripheral side and close to the tubular support part, compared to when fixed at a position far from the tubular support part, the elastic valve body and the opening member are positioned with high precision, and the bending stress due to external force applied in the pull-out direction of the tubular support part in relation to the outside holding part is also kept small, thereby advantageously ensuring strength at the fixing sites of the outside holding part as well.

A ninth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes inner and outer annular grooves that extend in a circumference direction respectively on both inner and outer surfaces of an outer periphery part of the elastic valve body, and a slim part positioned between bottom parts of the inner and outer annular grooves, and a tubular support part that is formed at an outer peripheral side of the slim part and projects inward and outward in an axial direction; the opening member includes a tube-shaped outside holding part overlapping an outer peripheral surface of the tubular support part and a tube-shaped inside holding part overlapping an inner peripheral surface of the tubular support part so that the outside holding part and the inside holding part are engaged with the respective annular grooves on the outer surface and the inner surface of the elastic valve body; the tubular support part is sandwiched and supported at a part projecting inward in the axial direction between the inside holding part and the outside holding part; and with the elastic valve body, the tubular support part has, at the part projecting inward in the axial direction, an axial direction dimension larger than an axial direction dimension of the center part of the elastic valve body.

With the medical valve constituted according to this mode, with the tubular support part of the elastic valve body, the projection height inward in the axial direction is ensured to be large, so that the same effect as that of the first mode is exhibited. Specifically, it is possible to ensure a large bearing capacity of the elastic valve body by the opening member, and to reduce the risk of the elastic valve body falling out inward in the axial direction.

A tenth mode of the present invention provides the medical valve according to any of the first to ninth modes, wherein the elastic valve body includes inner and outer annular grooves that extend in a circumference direction respectively on both inner and outer surfaces in the axial direction at the outer peripheral side of the center part, and the slim part is constituted between bottom parts of the inner and outer annular grooves, the outside holding part includes an outside engaging claw that enters the outer annular groove on the outer surface of the elastic valve body while the inside holding part includes an inside engaging claw that enters the inner annular groove on the inner surface of the elastic valve body, and an inner surface of a base end side of the inside engaging claw of the inside holding part inclines and expands inward in the axial direction so as to define an expanding inclined surface.

With the medical valve constituted according to this mode, the inner surface is inclined at the base end part of the inside engaging claw and expands inward in the axial direction. Thus, during insertion of the male connector, it is possible to ensure a broad internal space of the inside holding part into which the elastic valve body enters during elastic deformation. By so doing, elastic deformation of the elastic valve body is easily allowed during insertion of the male connector, and it is possible to reduce insertion resistance.

The inner surface shape at the tip part of the inside engaging claw is not limited in any way, but it is preferable that the tip side inner surface corner of the inside engaging claw be a convex curved surface, and furthermore, that at least a part of the outside engaging claw and the inside engaging claw mutually overlap when viewed in the axial direction, and that the curved surface of the inside engaging claw be positioned on the axial direction extension line of the radial direction inside end part of the outside engaging claw. By so doing, for example if the male connector is inserted so as to follow the inner peripheral surface of the outside engaging claw of the outside holding part or the like, and even if a large deformation occurs on the outer periphery part of the elastic valve body, it is possible to disperse concentration of push-in force of the male connector or local distortion of the elastic valve body by allowing it to escape along the curved surface of the inside engaging claw. As a result, for example even if the male connector is inserted decentered from the center of the elastic valve body, or inserted diagonally with an incline to the center axis of the elastic valve body, it is possible to suppress the occurrence of cracks or the like in the elastic valve body, and to improve durability.

An eleventh mode of the present invention provides the medical valve according to any of the first to tenth modes, wherein the outside holding part has a wall thickness that becomes gradually larger as it goes inward in the axial direction at least at an axial direction middle part for which a screw thread is not provided on an outer peripheral surface thereof, and the outside holding part gradually inclines outward in a radial direction as it goes inward in the axial direction, and each of the inner peripheral surface of the tubular support part at the part projecting inward in the axial direction and an inner peripheral surface of the inside holding part inclines at a sharper angle than an inner peripheral surface of the outside holding part and broadens inward in the axial direction, at least at a part further inward than a middle part in the axial direction.

With the medical valve constituted according to this mode, at the inside holding part and the outside holding part extending in the axial direction of the opening member, the thickness dimension of the base end part positioned inward in the axial direction, for which great stress occurs easily due to eternal force applied when the male connector is inserted or the like, is made large, so that the member strength and durability are improved. Also, the bearing capacity by the inside holding part and the outside holding part that sandwich and support the tubular support part from both the inner and outer sides operates even more effectively as a retaining resistance force on the base end side of the tubular support part which gradually becomes thicker. In fact, the inside holding part and the outside holding part that sandwich and support the base end side of the tubular support part also have the base end side made thicker, so that the bearing capacity on the base end side of the tubular support part is exhibited even more effectively. In addition, since the inner peripheral surface of the inside holding part broadens inward in the axial direction, it is also possible to ensure a large internal space of the inside holding part into which the elastic valve body elastically deforms and enters during insertion of the male connector.

A twelfth mode of the present invention provides the medical valve according to any of the first to eleventh modes, wherein the inside holding part includes a thin wall part at the axial direction middle part thereof with the radial direction thickness made smaller than those of both axial direction end parts thereof.

With the medical valve constituted according to this mode, at the thin wall part of the inside holding part, there is even more advantageous exhibition of the effect of increasing the bearing capacity in relation to the tubular support part exhibited based on being pressed by the elastic valve body toward the outer peripheral side when the male connector is inserted in the elastic valve body. Also, with this inside holding part, with the tip side that supports the slim part of the elastic valve body and the base end side for which the initiation stress is large, the respective radial direction thickness is sufficiently obtained. Thus, it is also possible to effectively ensure engaging force on the annular groove of the elastic valve body at the tip side, supporting strength at the base end side, and the like.

A thirteenth mode of the present invention provides the medical valve according to any of the first to twelfth modes, wherein the tubular support part includes an angle change part for which an inclination angle in the axial direction changes at the inner peripheral surface thereof on which the inside holding part is overlapped.

With the medical valve constituted according to this mode, at the angle change part provided at the inner peripheral surface of the tubular support part on which the inside holding part is overlapped, fallout resistance power of the tubular support part by the engaging action on the inside holding part is exhibited. In this way, in addition to the bearing capacity by sandwiching by the inside and outside holding parts, this engaging action will be exhibited. Accordingly, it is possible to more effectively prevent falling out of the elastic valve body from the opening member when inserting the male connector.

A fourteenth mode of the present invention provides the medical valve according to any of the first to thirteenth modes, wherein with the opening member, the inside holding part and the outside holding part are made to be separate members, and each tip end surface positioned inward in the axial direction of the inside holding part and the outside holding part is supported by the opening member main body.

A fifteenth mode of the present invention provides the medical valve according to the fourteenth mode, wherein the inside holding part is not joined to either the opening member main body or the outside holding part.

A sixteenth mode of the present invention provides the medical valve according to any of the first to fifteenth modes, wherein the outside holding part includes a step-shaped annular shoulder part broadening in the radial direction on the axial direction middle part thereof, and with the tubular support part of the elastic valve body, the tip of the part projecting inward in the axial direction projects further inward in the axial direction than the annular shoulder part.

With the medical valve constituted according to this mode, with the tubular support part of the elastic valve body, a large projection height is ensured inward in the axial direction. Thus, the same effect as with the first mode can be exhibited, and in particular, it is also possible to efficiently apply a large sandwiching force on the tubular support part by the outside holding part made substantially thicker at the annular shoulder part. Also, by combining with the third mode and the tenth mode described above, it is possible to broaden the internal space of the opening member. In specific terms, by combining with the third mode, with the tubular support part, the radial direction projecting part that expands to the outer peripheral side from the tip side of the part projecting inward in the axial direction can be skillfully arranged in a sandwiched and compressed state using the space made inside in the axial direction of the annular shoulder part.

A seventeenth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes inner and outer annular grooves that extend in a circumference direction respectively on both inner and outer surfaces of an outer periphery part of the elastic valve body, and an annular joining part positioned between bottom parts of the inner and outer annular grooves, and a tubular support part that is formed at an outer peripheral side of the annular joining part and projects inward and outward in an axial direction; the opening member includes a tube-shaped outside holding part overlapping an outer peripheral surface of the tubular support part and a tube-shaped inside holding part overlapping an inner peripheral surface of the tubular support part so that the outside holding part and the inside holding part are engaged with the respective annular grooves on the outer surface and the inner surface of the elastic valve body; the tubular support part has a projection height from the annular joining part inward in the axial direction larger than a projection height from the annular joining part outward in the axial direction; and the tubular support part is sandwiched and supported at a part projecting inward in the axial direction between the inside holding part and the outside holding part.

With the medical valve constituted according to this mode, the tubular support part of the elastic valve body ensures a large projection height inward in the axial direction, so that the same effect as that of the first mode can be exhibited. Specifically, it is possible to ensure a large bearing capacity of the elastic valve body by the opening member, and to reduce the risk of the elastic valve body falling out inward in the axial direction.

An eighteenth mode of the present invention provides a medical valve wherein a disk-shaped elastic valve body having a slit formed on a center part thereof is mounted on an opening member constituting an opening part of a fluid flow path, and the elastic valve body is configured to enable a male connector to be repeatedly inserted and removed through the slit, the medical valve being characterized in that: the elastic valve body includes inner and outer annular grooves that extend in a circumference direction respectively on both inner and outer surfaces of an outer periphery part of the elastic valve body, and an annular joining part positioned between bottom parts of the inner and outer annular grooves, and a tubular support part that is formed at an outer peripheral side of the annular joining part and projects inward and outward in an axial direction; the opening member includes a tube-shaped outside holding part overlapping an outer peripheral surface of the tubular support part and a tube-shaped inside holding part overlapping an inner peripheral surface of the tubular support part so that the outside holding part and the inside holding part are engaged with the respective annular grooves on the outer surface and the inner surface of the elastic valve body; with the tubular support part, a tip of a part projecting inward in the axial direction is positioned further inward in the axial direction than an axial direction inner surface of the center part of the elastic valve body; and the tubular support part is sandwiched and supported at the part projecting inward in the axial direction between the inside holding part and the outside holding part.

With the medical valve constituted according to this mode as well, the tubular support part has a large projection height inward in the axial direction, and the tubular support part is sandwiched and supported at the part projecting inward in the axial direction between the inside holding part and the outside holding part of the opening member. Therefore, roughly the same as with the medical valve of the seventeenth mode, the bearing capacity of the elastic valve body by the opening member is largely ensured, and falling out of the elastic valve body inward in the axial direction is inhibited.

Effect of the Invention

With the medical valve according to the constitution of the present invention, by the action of friction or the like between the inside/outside holding parts sandwiching and supporting the tubular support part and the elastic valve body, it is possible to make the bearing capacity by the opening member greater, and possible to effectively prevent falling out of the elastic valve body during insertion of the male connector or the like.

EMBODIMENTS FOR CARRYING OUT THE INVENTION

Figure 1:
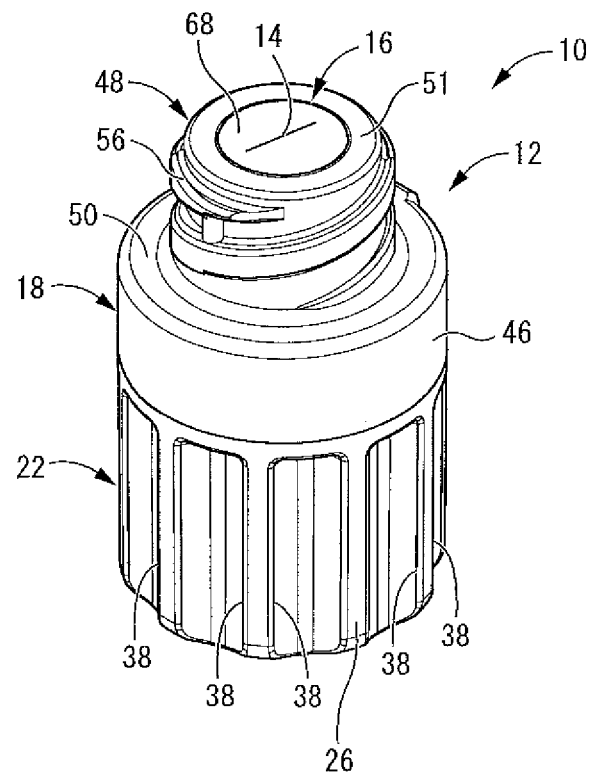
FIG. 1 is a perspective view of a medical valve as a first embodiment of the present invention.
Figure 2:
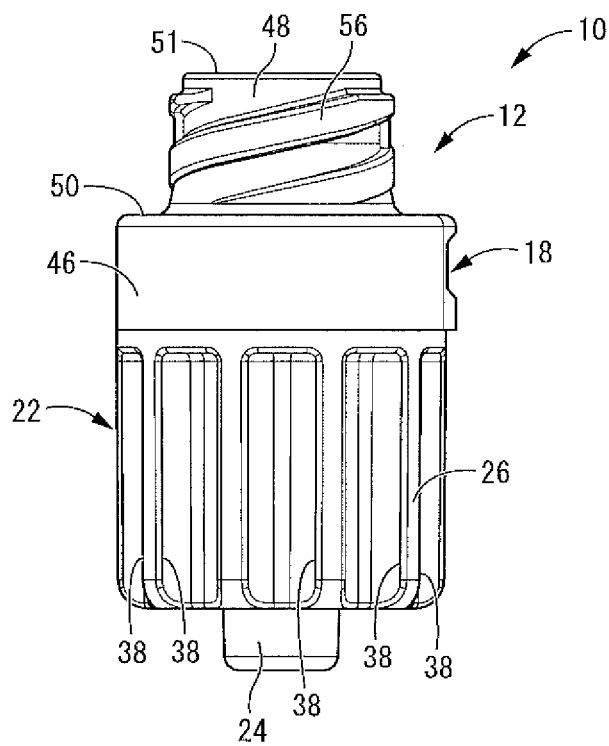
FIG. 2 is a front view of the medical valve shown in FIG. 1.
Figure 3:
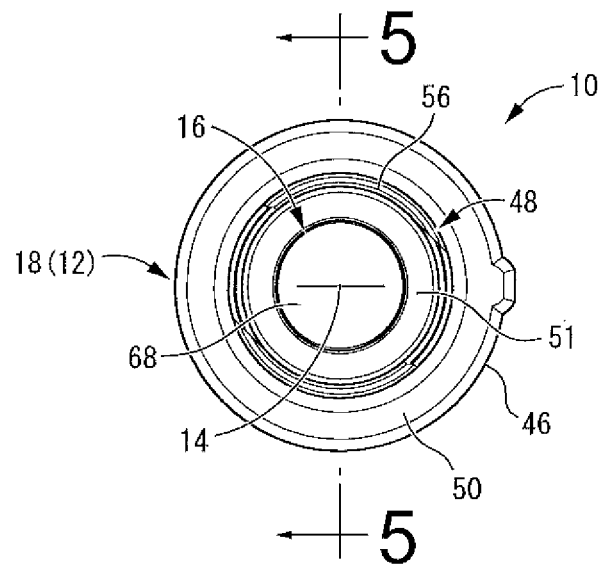
FIG. 3 is a plan view of the medical valve shown in FIG. 1.
Figure 4:
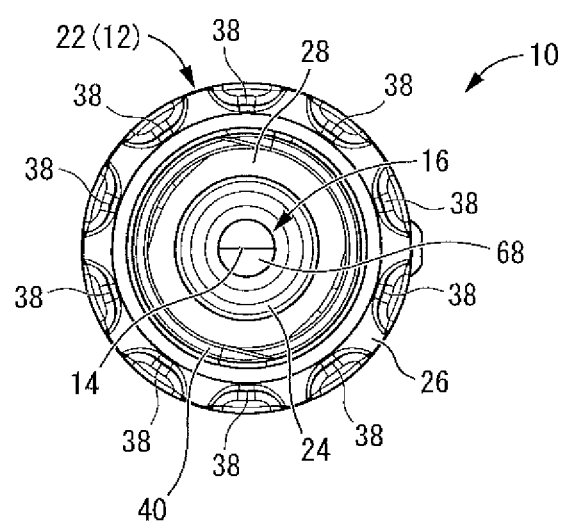
FIG. 4 is a bottom view of the medical valve shown in FIG. 1.

Following, we will describe embodiments of the present invention while referring to the drawings.

First, in FIG. 1 to 6, a medical valve 10 is shown as a first embodiment of the present invention. The medical valve 10 has a constitution wherein a roughly disk-shaped elastic valve body 16 on which a slit 14 is formed is mounted on an opening member 12 constituting an opening part of a fluid flow path, and a male connector can be repeatedly inserted and removed through the slit 14 of this elastic valve body 16. With the description below, the vertical direction and the directions outward/outside and inward/inside in the axial direction all mean the vertical direction in FIG. 2.

In more detail, the opening member 12 overall has a roughly tubular shape, and is constituted having an assembled structure of three separate members including an outside holding part 18 and an inside holding part 20, both of which are roughly tube-shaped, and a valve housing main body 22 as an opening member main body. Specifically, the opening member 12 is constituted by the inside holding part 20 being attached without bonding to the top of the valve housing main body 22, the outside holding part 18 being overlapped on the outer peripheral side of the inside holding part 20, and the valve housing main body 22 and the outside holding part 18 being adhered.

With the valve housing main body 22, a peripheral wall part 26 is provided on the outer peripheral side of a center tube-shaped part 24 extending vertically in the axial direction, and by the respective top end parts being connected by an upper bottom part 28, the valve housing main body 22 is constituted. The axial direction dimension of this center tube-shaped part 24 is made larger than the axial direction dimension of the peripheral wall part 26, and the center tube-shaped part 24 projects downward inside the peripheral wall part 26.

Furthermore, on the top surface of the upper bottom part 28, a circular fixing groove 34 is formed so as to extend across the entire circumference in the circumference direction at the radial direction middle part. Then, this fixing groove 34 opens at the top surface of the upper bottom part 28. A specified inclination angle is given to the opposite inner surfaces of both inner and outer walls of the fixing groove 34, and the cross section shape of the fixing groove 34 gradually expands in diameter toward the opening direction.

Also, as will be described later, the end parts of each base end side (inside in the axial direction) of the outside holding part 18 and the inside holding part 20 are engaged on the fixing groove 34 of the upper bottom part 28. Also, the wall part on the outer peripheral side of the fixing groove 34 is used as an annular supporting wall 35 that positions the outside holding part 18 and the inside holding part 20 in relation to the valve housing main body 22 in the radial direction.

Yet further, a projecting part for welding 36 projecting upward is integrally formed on the top surface of the supporting wall 35. Then, as is described later, the outside holding part 18 is overlapped on the top surface of the supporting wall 35 of the valve housing main body 22, and by adhering the projecting part for welding 36 using ultrasonic welding, the outside holding part 18 is adhered to the valve housing main body 22. The projecting part for welding 36 of the valve housing main body 22 is substantially melted and lost in the product state, but in FIG. 6, to make it easier to explain and understand, the projecting part for welding 36 is shown virtually by a dotted line. Also, the projecting part for welding 36 can also be provided on the outside holding part 18 overlapped on the supporting wall 35 of the valve housing main body 22.

Also, while a circular step surface 37 that broadens in the axis-perpendicular direction is formed on the outer peripheral surface near the top end of the peripheral wall part 26, below the step surface 37, a plurality of recesses 38 (ten with this embodiment) extending in the axial direction are formed across the entire periphery in the circumference direction. By giving dents and bumps to the outer peripheral surface using these plurality of recesses 38, it is possible for the user to easily grasp the outer peripheral surface of the valve housing main body 22 of the medical valve 10. Meanwhile, a lock groove 40 is formed on the inner peripheral surface of the peripheral wall part 26, making it possible to connect a Luer lock connector or the like.

Above the valve housing main body 22 having this constitution, the outside holding part 18 of the outer peripheral side and the inside holding part 20 of the inner peripheral side are attached as separate parts. The axial direction top end of the outside holding part 18 is positioned further upward in the axial direction than the axial direction top end of the inside holding part 20. Also, the axial direction bottom end of the outside holding part 18 is overlapped in the axial direction on the step surface 37 of the valve housing main body 22.

The outside holding part 18 has a structure wherein a lower large diameter tube part 46 and an upper small diameter tube part 48 are integrally connected by a step-shaped annular shoulder part 50 that broadens in the radial direction. Said another way, the annular shoulder part 50 is provided at the axial direction middle part of the outside holding part 18, and the upper side of this annular shoulder part 50 is used as the small diameter tube part 48, while the lower side thereof is used as the large diameter tube part 46. As can be understood from the explanation given later, with this embodiment, the outside holding part as a member that supports the elastic valve body 16 between it and the inside holding part 20 is constituted by the small diameter tube part 48 for which the annular shoulder part 50 is formed on the axial direction base end part. Thus, the large diameter tube part 46 is understood to operate as an auxiliary part for fixing of the outside holding part to the valve housing main body 22.

Here, the inner peripheral surface and outer peripheral surface of the small diameter tube part 48 have a tapered shape for which it becomes gradually smaller in diameter as it goes outward in the axial direction. Also, with the small diameter tube part 48, at the base end part (bottommost part)

for which the inner diameter dimension is greatest, the inner diameter dimension is smaller than the opening diameter of the outer peripheral side wall of the fixing groove 34 while being larger than the opening diameter of the inner peripheral side wall of the fixing groove 34. Meanwhile, with the small diameter tube part 48, at the tip part (topmost part) for which the inner diameter dimension is smallest, the inner diameter dimension is roughly equal to the outer diameter dimension of the elastic valve body 16.

Furthermore, the top part of the small diameter tube part 48 of the outside holding part 18 is used as a circular tip wall part 51 that broadens in a bent state to the inner peripheral side, and at the inner periphery edge part of the tip wall part 51, an outside engaging claw 52 is formed extending downward so as to be folded back inward in the axial direction. With this embodiment, the outside engaging claw 52 is formed in a circular shape extending across the entire periphery in the circumference direction, and at the outer peripheral side of the outside engaging claw 52, an outside holding groove 54 extending in the circumference direction having a designated width in the radial direction is formed as a circular groove opening downward in the axial direction.

On the outer peripheral surface of the small diameter tube part 48, a male screw part 56 is formed with which a female screw part of a Luer lock connector is screwed together, for example. The male screw part 56 is a double thread screw that can connect with a female screw part of a Luer lock connector regulated by ISO594, for example. To ensure sufficient screwing together with the female screw part of the Luer lock connector, the annular shoulder part 50 is preferably positioned downward by 3 mm or more from the upper end of the male screw part 56 provided on the outer peripheral surface of the outside holding part 18 (small diameter tube part 48).

Also, with the outer diameter dimension of the outside holding part 18, in a case where the male screw part 56 like that of this embodiment is not formed, the outer diameter of the small diameter tube part 48 is preferably set within a range from 5.5 to 7.2 mm, and where the male screw part 56 is formed as with this embodiment, the outer diameter of the small diameter tube part 48 including a screw thread is preferably set within a range from 7.2 to 8.5 mm.

Yet further, with the small diameter tube part 48, at the axial direction middle part between the annular shoulder part 50 on the base end side and the outside holding groove 54 on the tip side, the thickness dimension of the peripheral wall for which the screw thread for the male screw part 56 is not formed changes to be gradually larger toward the base end side from the tip side in the axial direction. Specifically, at the axial direction middle part of the small diameter tube part 48, the inclination is sharper with the inner peripheral surface than with the outer peripheral surface, and the inclination angle in relation to the axis-perpendicular direction is made larger.

Furthermore, at the lower surface of the annular shoulder part 50 of the outside holding part 18, an engaging groove 58 that opens downward is formed. Also, at the inner periphery edge part of the annular shoulder part 50, a locking convex part 60 is formed projecting downward in the axial direction. In particular with this embodiment, the engaging groove 58 is used as the annular groove extending across the entire periphery in the circumference direction, and the locking convex part 60 is also used as the annular convex part extending across the entire periphery in the circumference direction.

With this embodiment, as the end surface of the axial direction base end side of the small diameter tube part 48, the bottom surface of the engaging groove 58 is overlapped and supported on the top surface of the supporting wall 35 of the valve housing main body 22. Specifically, with the valve housing main body 22, the base end side outer peripheral surface of a tubular support part 70 described later of the elastic valve body 16 is positioned and supported at the inner peripheral surface of the supporting wall 35, and the outside holding part 18 is fixed by welding to the valve housing main body 22 by the projecting part for welding 36 projecting on the top surface of the supporting wall 35 positioned near on the outer peripheral side in relation to the supporting surface of the tubular support part 70.

Figure 5:
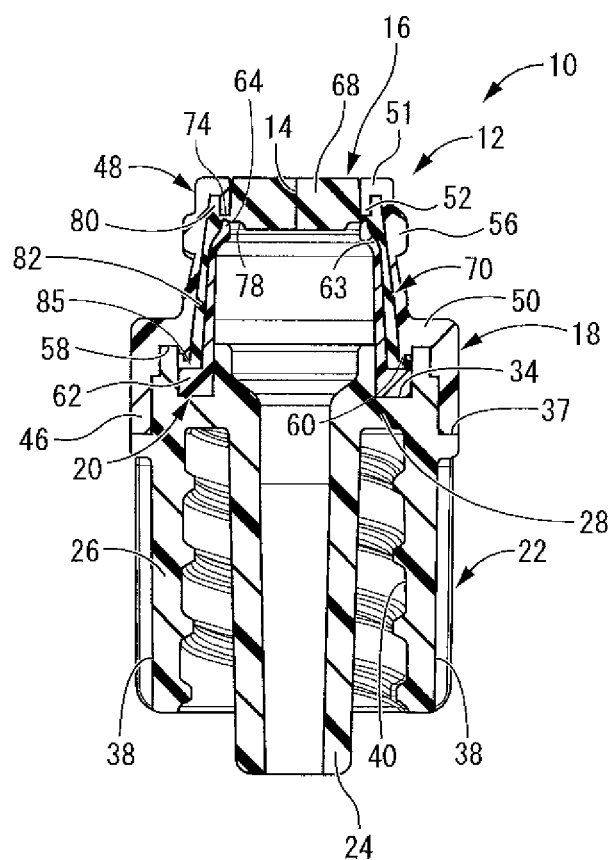
FIG. 5 is a cross section view taken along line 5-5 of FIG. 3.

Meanwhile, the inside holding part 20 has an overall tapered tube shape for which the diameter becomes smaller as it goes from inside to outside in the axial direction, and the bottom end part of the inside holding part 20 is used as an annular base end part 62 as a radial direction projecting part extending to the outer peripheral side with a fixed thickness dimension (vertical direction in FIG. 5).

This annular base end part 62 has a size and shape that fits into the fixing groove 34 of the valve housing main body 22, and the axial direction inside end surface of the inside holding part 20 including the annular base end part 62 is overlapped and supported on the bottom surface of the fixing groove 34. The axial direction thickness dimension of the annular base end part 62 is smaller than the depth dimension of the fixing groove 34, the axial direction inside end part of the small diameter tube part 48 of the outside holding part 18 fits into the opening part of the fixing groove 34, and is fit to the wall surface of the outer peripheral side of the fixing groove 34. By so doing, with this embodiment, each axial direction inside end part of the inside holding part 20 and the outside holding part 18 is fit into the fixing groove 34, and accordingly, the inside holding part 20 and the outside holding part 18 are positioned in the radial direction in relation to the valve housing main body 22.

Also, at the axial direction top side part of the inside holding part 20, an annular receiving seat part 63 narrowing to the inner peripheral side is formed with a gooseneck shaped curved cross section. Also, on the inner periphery edge part of the receiving seat part 63, an annular inside engaging claw 64 projecting upward in the axial direction is formed. Specifically, a part from the base end side inner surface of the inside engaging claw 64 to the inner surface of the receiving seat part 63 is an expanding inclined surface 65 for which the inner diameter gradually becomes larger inward in the axial direction. By providing this expanding inclined surface 65, during insertion of the male connector (Luer) described later into the elastic valve body 16, escape areas for both side parts of the slit 14 which is pressed apart while being pressed inward are advantageously ensured inside the inside holding part 20, and the insertion resistance of the male connector and the like is reduced. The tip end surface of the inside engaging claw 64 has a convex curved cross section shape for which the end edge part of the inner peripheral side has the corners rounded. For this curved cross section shape, for example preferably a round shape having a roughly fixed curvature radius is used, but it is also possible to use one for which the curvature radius differs in parts.

Also, the inside engaging claw 64 of the inside holding part 20 is positioned across a gap in the axial direction in opposition to the outside engaging claw 52 of the outside holding part 18. The inside engaging claw 64 and the outside engaging claw 52 preferably have at least a portion overlapping each other when viewed in the axial direction, and would suitably mutually overlap when viewed in the axial direction over an area of half or more in the radial direction. In particular, with this embodiment, the round shaped curved surface provided on the inner peripheral side corner of the inside engaging claw 64 is positioned on the axial direction extension line of the inner periphery end (radial direction inside end part) of the outside engaging claw 52.

Also, the receiving seat part 63 of the inside holding part 20 is arranged roughly in opposition to the tip wall part 51 of the outside engaging claw 52 in the axial direction.

Furthermore, the inside holding part 20 has the wall thickness dimension of its periphery wall differ in the axial direction. In particular with this embodiment, the receiving seat part 63 and the inside engaging claw 64 are formed by the tip side positioned outward in the axial direction being made thick. Also, the part positioned near the bottom of the receiving seat part 63 is used as a thin wall part 66 whose thickness dimension is smallest, and the thickness gradually increases as it goes inward in the axial direction from this thin wall part 66. Specifically, with the small diameter tube part 48, at the axial direction middle part between the receiving seat part 63 on the tip end and the annular base end part 62 on the base end, the inner peripheral surface expands in a taper shape downward in the axial direction at a sharper inclination angle than the outer peripheral surface. Changes in the thickness dimension in the axial direction with the inside holding part 20 are given continuously and smoothly by the inner and outer peripheral surfaces being curved or the like in the axial direction.

Also, the outer diameter dimension of the inside holding part 20 is smaller than the inner diameter dimension of the outside holding part 18, and as shown in FIG. 5 and the like, a space for mounting the elastic valve body 16 is formed between the outside holding part 18 and the inside holding part 20.

The single item state of the elastic valve body 16 to be mounted in this mounting space is shown in FIGS. 7 to 10. The elastic valve body 16 is roughly disk-shaped, and the slit 14 is formed in a center part 68. Also, the tubular support part 70 is provided so as to project inward and outward in the axial direction on the outer periphery part of the elastic valve body 16. The outer peripheral surface of the tubular support part 70 is overlapped on the inner peripheral surface of the outside holding part 18, while the inner peripheral surface of the tubular support part 70 is overlapped on the outer peripheral surface of the inside holding part 20. Furthermore, by the center part 68 and the tubular support part 70 being connected by an annular joining part 72 extending across the entire periphery in the circumference direction, the elastic valve body 16 is formed as an integrally molded article.

With regard to the elastic valve body 16, with the male connector in a non-inserted state shown in FIG. 5, the top end surface of the center part 68 and the top end surface of the opening member 12 are positioned on the same plane. Also, with this embodiment, the slit 14 is a straight line piercing through the thickness direction of the elastic valve body 16, but it is also possible to use three or more slits extending radially from the center or the like.

The annular joining part 72 is formed by making the thickness dimension smaller than that of the center part 68 of the elastic valve body 16. Specifically, at the outer periphery part of the elastic valve body 16, groove-shaped outer annular groove 74 and inner annular groove 76 are formed respectively on the axial direction outer surface and inner surface so as to extend across the entire periphery in the circumference direction. A constriction is formed at the outer periphery part of the elastic valve body 16 by these annular grooves 74 and 76, and this constricted part, specifically the part between the bottom parts of the annular grooves 74 and 76 in the axial direction is used as the annular joining part 72. Therefore, with the elastic valve body 16, at further to the outer peripheral side than the center part 68, the slim part that is thinner than the center part 68 is constituted by the annular joining part 72.

The respective shapes of both annular grooves 74 and 76 roughly correspond to the outside engaging claw 52 and the inside engaging claw 64, and the outside and inside engaging claws 52 and 64 are allowed to be fitted. Also, a recess groove part 78 is formed on the wall part on the inner peripheral side of the inner annular groove 76, and the inner surface shape of the recess groove part 78 roughly corresponds to the inner peripheral surface shape of the tip of the inside engaging claw 64. By so doing, during insertion of the male connector described later, the inner peripheral surface of the tip of the inside engaging claw 64 and the inner surface of the recess groove part 78 overlap and abut, reducing the risk of formation of a gap at the fluid flow path 90 within the medical valve 10.

Also, the tubular support part 70 connected to the outer peripheral side of the annular joining part 72 has a shape corresponding to the mounting space between the outside holding part 18 and the inside holding part 20. Specifically, the tubular support part 70 is constituted including an upper support part 80 projecting outward in the axial direction from the annular joining part 72 and a lower support part 82 projecting inward in the axial direction.

In other words, the upper support part 80 has a designated axial direction dimension and projects upward from the annular joining part 72, and the radial direction width dimension thereof is made roughly the same as or slightly bigger than the radial direction width dimension of the outside holding groove 54. Also, while the inner peripheral surface shape of the upper support part 80 roughly corresponds to the outer peripheral surface shape of the outside engaging claw 52, the outer peripheral surface shape of the upper support part 80 roughly corresponds to the inner peripheral surface shape of the small diameter tube part 48. Furthermore, the lower support part 82 has a designated axial direction dimension and projects downward from the annular joining part 72, and with this embodiment, during attachment of the opening member 12 and the elastic valve body 16, the lower support part 82 projects as far as a position below the annular shoulder part 50 of the outside holding part 18. Also, while the inner peripheral surface shape of the lower support part 82 roughly corresponds to the outer peripheral surface shape of the inside holding part 20, the outer peripheral surface shape of the lower support part 82 corresponds to the inner peripheral surface shape of the small diameter tube part 48.

By so doing, the inner and outer peripheral surfaces of the lower support part 82 is sandwiched and supported in the radial direction which is the thickness direction between the inside holding part 20 and the outside holding part 18 (small diameter tube part 48). Here, the outer peripheral surface of the inside holding part 20 is a sharply inclined surface having an inclination angle in the axial direction larger than that of the inner peripheral surface of the outside holding part 18. Thus, the lower support part 82, which is arranged in a housed state sealed between opposite faces in the radial direction of the inside and outside holding parts 20 and 18, has a wall thickness dimension that becomes gradually larger as it goes inward in the axial direction.

Specifically, the outer peripheral surface of the tubular support part 70 is a tapered inclined surface that gradually expands inward in the axial direction at roughly the same inclination angle as that of the inner peripheral surface of the outside holding part 18 (small diameter tube part 48) across the entirety of the upper support part 80 and the lower support part 82. Also, with regard to the inner peripheral surface of the tubular support part 70, the inner peripheral surface of the upper support part 80 is an inclined surface that expands slightly outward in the axial direction, roughly corresponding to the outer peripheral surface of the outside engaging claw 52. Meanwhile, the inner peripheral surface of the lower support part 82 has a shape roughly corresponding to the outer peripheral surface shape of the inside holding part 20.

Figure 6:
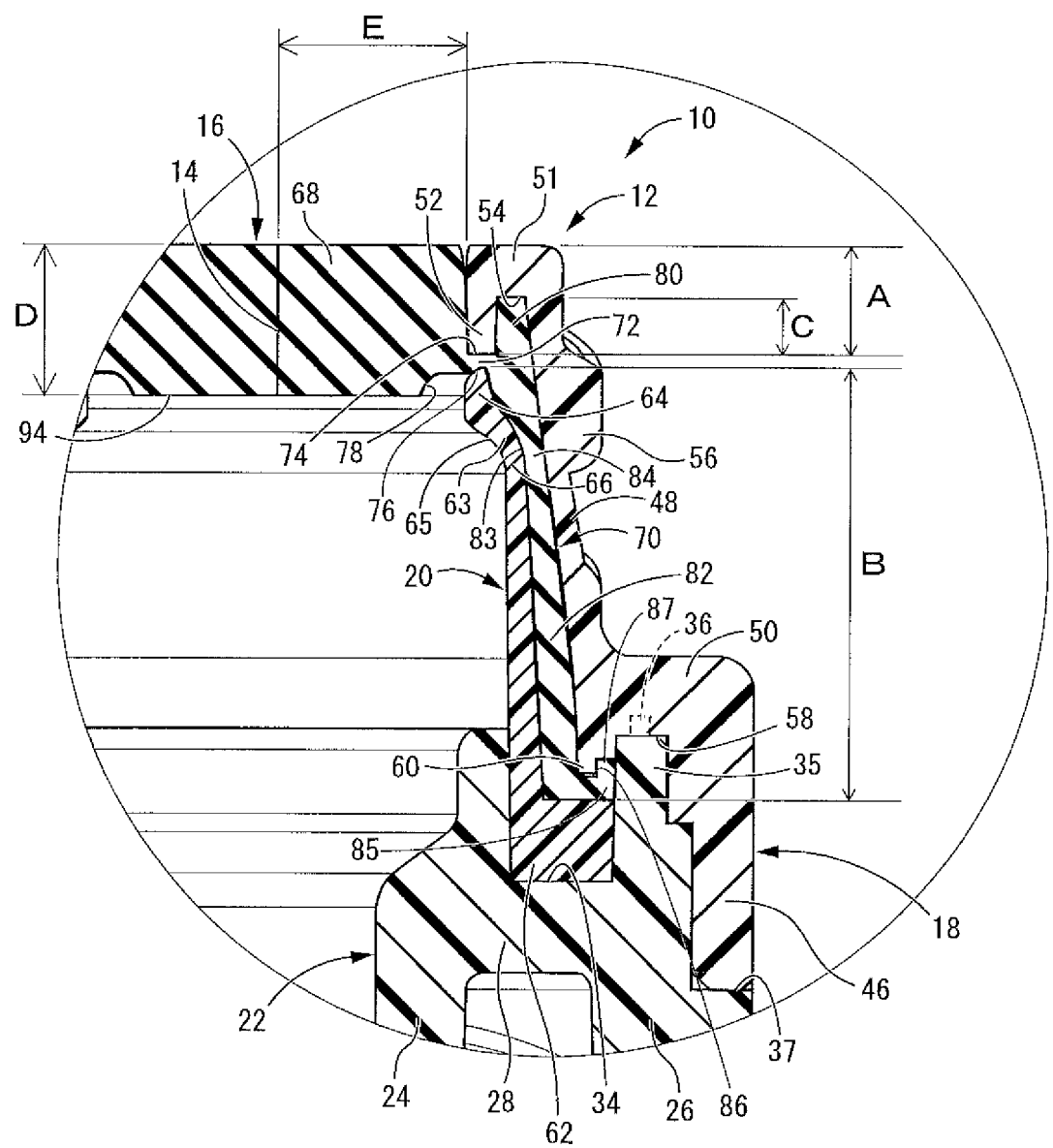
FIG. 6 is a cross section view with the key parts in FIG. 5 enlarged.
Figure 7:
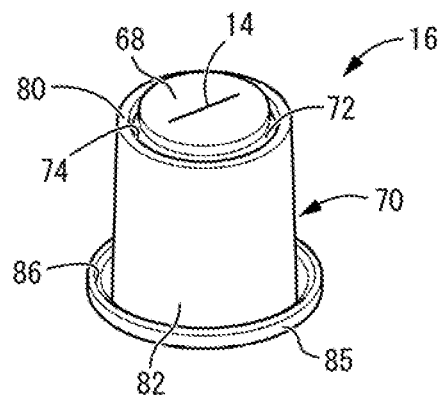
FIG. 7 is a perspective view showing an elastic valve body constituting the medical valve shown in FIG. 1.
Figure 8:
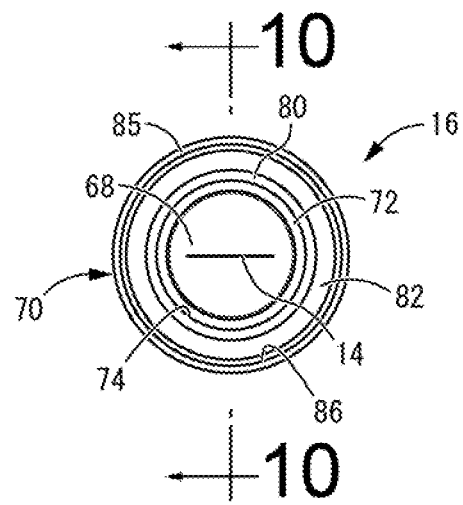
FIG. 8 is a plan view of the elastic valve body shown in FIG. 7.
Figure 9:
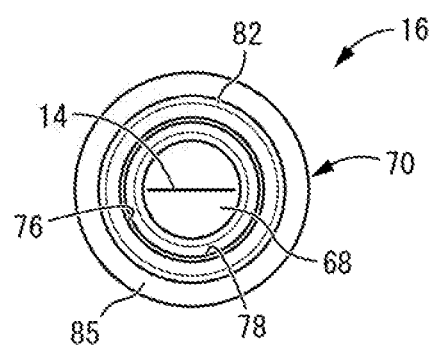
FIG. 9 is a bottom view of the elastic valve body shown in FIG. 7.
Figure 10:
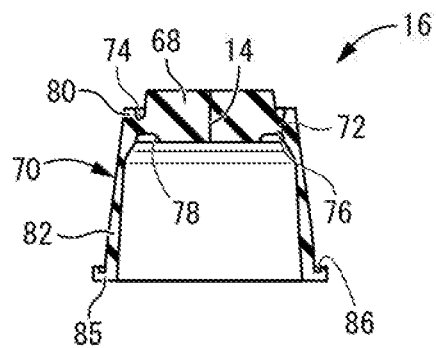
FIG. 10 is a cross section view taken along line 10-10 of FIG. 8.

In specific terms, on the inner peripheral surface of the lower support part 82, an angle change part 83 for which the inclination angle in the axial direction changes is provided so as to be positioned near the annular joining part 72. This angle change part 83 has a recessed round surface as shown in FIG. 6, and at this angle change part 83 having a round surface, the thickness dimension of the lower support part 82 is made to be smallest and is used as a thin part 84. Also, the part positioned outward in the axial direction from the angle change part 83 (upward in FIG. 6) is made thicker and is connected to the annular joining part 72, and this thick part is supported by the receiving seat part 63 of the inside holding part 20. Meanwhile, at the part positioned inward in the axial direction from the angle change part 83 (downward in FIG. 6), the inner peripheral surface of the lower support part 82 is a tapered inclined surface that gradually expands inward in the axial direction at roughly the same inclination angle as that of the outer peripheral surface of the inside holding part 20. In other words, the inner peripheral surface of the lower support part 82 and the inner peripheral surface at the axial direction middle part of the inside holding part 20 have a greater inclination angle than that of the inner peripheral surface of the small diameter tube part 48 of the outside holding part 18.

Also, with the lower support part 82, the diameter dimension of the projecting direction tip side (downward in FIG. 5) is made larger than that of the projecting direction base end side (upward in FIG. 5), and a flange part 85 as a radial direction projecting part broadening to the outer peripheral side is integrally formed on the projecting tip part (lowest end in the axial direction). Specifically, with the lower support part 82 of this embodiment, while the thickness dimension is made to be smallest at the thin part 84, the thickness dimension (radial direction dimension) at the flange part 85 positioned further inward in the axial direction than the thin part 84 is made to be biggest. Therefore, with this embodiment, at the lower support part 82, the thick part is formed including the flange part 85. The radial direction width dimension of this flange part 85 is roughly equal to the radial direction width dimension at the top surface of the annular base end part 62 of the inside holding part 20. Furthermore, on the top surface of the flange part 85, a locking recess 86 extending across the entire periphery in the circumference direction is formed at a position and size corresponding to the locking convex part 60 of the outside holding part 18, and the outer peripheral side of this locking recess 86 is used as a locking projection 87 projecting outward in the axial direction.

The outside holding part 18, the inside holding part 20, and the valve housing main body 22 constituting the opening member 12 of this embodiment are each preferably formed from material having strength that can reliably hold the elastic valve body 16, and a thermoplastic resin can be suitably used. Also, the elastic valve body 16 is formed from a material having elasticity, and considering airtightness and resealability, preferably a synthetic rubber such as isoprene rubber, silicone rubber or the like, natural rubber, or a thermoplastic elastomer or the like is used.

Also, with the elastic valve body 16, the outer diameter dimension at the top end part of the upper support part 80 is preferably set within a range from 5.0 to 7.0 mm.

Also, the thickness dimension of the center part 68 of the elastic valve body 16 is preferably set within a range from 1.0 to 4.0 mm. This is because if the thickness dimension of the center part 68 is smaller than 1.0 mm, there is the risk that there will be insufficient sealing properties when the syringe or the like is not inserted. On the other hand, if the thickness dimension is greater than 4.0 mm, insertion resistance of the male connector becomes greater, and there is the risk of the insertion operation being difficult.

With this embodiment, the inside holding part 20 is attached to the valve housing main body 22 in a shape as noted above without being bonded. Specifically, the annular base end part 62 of the inside holding part 20 is fit into the fixing groove 34 formed on the opening side end part of the valve housing main body 22, and is positioned in the radial direction. Also, the flange part 85 of the elastic valve body 16 is overlapped on the top surface of the annular base end part 62, and the inside engaging claw 64 of the inside holding part 20 is pressed into the inner annular groove 76 of the elastic valve body 16 so as to dig into it.

In this state, the outside holding part 18 is overlapped from outside in the axial direction, and as necessary, the outside holding part 18 is pressed in the axial direction on the valve housing main body 22. By so doing, the annular shoulder part 50 of the outside holding part 18 is overlapped in an abutted state on the projecting part for welding 36 projecting on the supporting wall 35 of the upper bottom part 28 of the valve housing main body 22. Also, by operating the ultrasonic energy with concentration on the projecting part for welding 36 by placing the horn of the ultrasonic welding device while pressing the abutting site against the projecting part for welding 36 in the axial direction, the projecting part for welding 36 and the abutting site are welded, and the projecting part for welding 36 is substantially melted and lost so that adhering is completed in a state with the annular shoulder part 50 of the outside holding part 18 overlapped on the upper bottom part 28 of the valve housing main body 22. When doing ultrasonic welding, the axial direction positioning of the valve housing main body 22 and the outside holding part 18 can be regulated by, in accordance with melting loss of the projecting part for welding 36, a rapid increase in the abutting surface area between the supporting wall 35 and the annular shoulder part 50, the end surface of the large diameter tube part 46 of the outside holding part 18 abutting the step surface 37 of the valve housing main body 22, or the like.

As a result, in the product state with the ultrasonic welding completed, the step surface 37 provided on the valve housing main body 22 and the bottom end surface of the large diameter tube part 46 of the outside holding part 18 are substantially abutted, and the upper bottom surface of the engaging groove 58 provided on the annular shoulder part 50 and the outer wall upper surface of the fixing groove 34 are in a roughly abutted state. Also, the locking convex part 60 provided on the inner surface of the outside holding part 18 is fit into and locked with the locking recess 86 provided on the elastic valve body 16, and the locking projection 87 of the elastic valve body 16 is fit into the fixing groove 34 of the valve housing main body 22 and locked to the inner peripheral surface of the supporting wall 35.

Furthermore, the upper support part 80 of the tubular support part 70 is pressed into the outside holding groove 54 of the outside holding part 18 to be supported, and the outside engaging claw 52 of the outside holding part 18 is pressed into the outer annular groove 74 of the elastic valve body 16 so as to dig into it. In this state, the medical valve 10 of this embodiment is constituted by the upper bottom surface of the engaging groove 58 and the outer wall top surface of the fixing groove 34 being adhered. The adherence of the upper bottom surface of the engaging groove 58 and the outer wall top surface of the fixing groove 34 is preferably done using ultrasonic welding utilizing the projecting part for welding 36 as described above, but for example it is also possible to use adhesion that does not utilizing the projecting part for welding.

Specifically, with this embodiment, the lower support part 82 of the tubular support part 70 is sandwiched and supported between the outside holding part 18 and the inside holding part 20. Also, by adhering the outside holding part 18 to the valve housing main body 22 by pressing in the axial direction, the inside holding part 20 positioned inward in the axial direction of the outside holding part 18 is supported with restraint in a non-adhered mode without bonding or the like on either the valve housing main body 22 or the outside holding part 18 or the like, thus being attached in a fixed manner.

Furthermore, by the locking convex part 60 of the outside holding part 18 being fit into the locking recess 86 of the flange part 85, and the outside holding part 18 being pressed from outside in the axial direction on the valve housing main body 22 to be adhered thereto, the flange part 85 of the elastic valve body 16 is sandwiched and supported between the outside holding part 18 and the annular base end part 62 of the inside holding part 20 in the axial direction. Specifically, with this embodiment, the elastic valve body 16 is not bonded but is positioned and fixed in the radial direction and the axial direction with respect to the opening member 12.

Here, in an attached state of the inside and outside holding parts 20 and 18 to the valve housing main body 22, the radial direction distance between the opposite surfaces of the inside and outside holding parts 20 and 18, which are overlapped on the inner and outer peripheral surfaces of the lower support part 82 of the elastic valve body 16, is roughly the same or slightly larger than the radial direction thickness dimension of the lower support part 82 of the elastic valve body 16 before attachment. By so doing, in the attached state, the lower support part 82 of the elastic valve body 16 is made not to be compressed by the inside and outside holding parts 20 and 18.

In addition, in the attached state of the inside and outside holding parts 20 and 18 on the valve housing main body 22, the axial direction distance between the opposite surfaces of the annular base end part 62 of the inside holding part 20 and the axial direction inside end part of the small diameter tube part 48 of the outside holding part 18, which are overlapped on both axial direction surfaces of the flange part 85 of the elastic valve body 16, is smaller than the axial direction thickness dimension of the flange part 85 of the elastic valve body 16 before attachment. By so doing, in the attached state, an effective bearing capacity is always exhibited with compression force by the inside and outside holding parts 20 and 18 applied to the flange part 85 of the elastic valve body 16.

Also, with the elastic valve body 16 of this embodiment, at the tubular support part 70, the axial direction length of the lower support part 82 (B in FIG. 6) is made greater than the axial direction length of the upper support part 80 (C in FIG. 6). In particular with this embodiment, in the attached state of the opening member 12 and the elastic valve body 16 having the shape described above, the distance B (see FIG. 6) from the lower surface of the annular joining part 72 to the axial direction inside end of the lower support part 82 is made greater than the distance A (see FIG. 6) from the top surface of the annular joining part 72 to the axial direction outside end of the outside holding part 18 (A<B). Specifically, the axial direction dimension B of the lower support part 82 is made greater than the axial direction dimension A which is assumed to be maximum for the upper support part 80.

Yet further, with this embodiment, the axial direction length (B) of the lower support part 82 is made greater than the axial direction length (D in FIG. 6) of the center part 68 of the elastic valve body 16 (B>D). Furthermore, the axial direction length (B) of the lower support part 82 is made greater than the radius of the center part 68 (E in FIG. 6) of the elastic valve body 16 (B>E).

Figure 11:
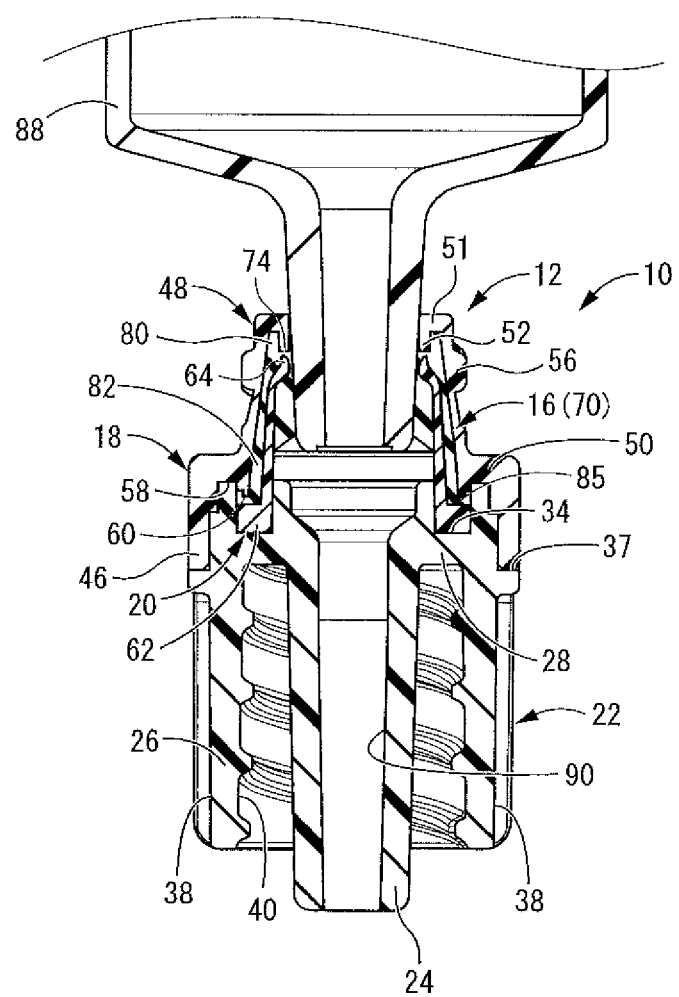
FIG. 11 is a view suitable for explaining the state with a male connector inserted in the medical valve shown in FIG. 1.

Furthermore, FIG. 11 shows a state for which a tip part of the syringe 88 serving as the male connector is inserted in the medical valve 10 constituted as described above. Specifically, by inserting the tip part of the syringe 88 in the elastic valve body 16, the slit 14 is opened, and the center part 68 of the elastic valve body 16 is pressed inward in the axial direction to be elastically deformed. By so doing, a fluid flow path 90, which goes from a catheter or the like (not illustrated) to inside the human body via the interior of the syringe 88 and the interior of the medical valve 10, is put in a communicating state. Said another way, by the syringe 88 being inserted in the elastic valve body 16 mounted on the opening member 12 constituting the opening part of the fluid flow path 90, the slit 14 is opened and the fluid flow path 90 is put in a communicating state.

Here, in the state with the syringe 88 inserted, a push-in force inward in the axial direction is generated on the elastic valve body 16. In relation to this push-in force, with the medical valve 10 of this embodiment, the axial direction projection dimension B of the lower support part 82 is made large, and the area of the elastic valve body 16 supported by the opening member 12 is ensured to be large. Thus, there is a decrease in the risk of the elastic valve body 16 falling out from the medical valve 10.

In particular, by making the projection dimension inward in the axial direction large, it is possible to make the friction greater between the opening member 12 and the lower support part 82 in relation to the tensile force outward in the axial direction which is applied to the lower support part 82. Accordingly, combined with the hooking operation of the elastic valve body 16 by the inside engaging claw 64, the effect of preventing falling out of the elastic valve body 16 from the medical valve 10 can be efficiently exhibited.

In particular with the present invention, by the lower support part 82 of the tubular support part 70 projecting further inward in the axial direction than a valve internal surface 94 (see FIG. 6) in the axial direction of the round-disk shaped center part 68 of the elastic valve body 16 where the slit 14 is formed, and which broadens in a roughly fixed axial direction thickness, it is possible to effectively apply the bearing capacity by the inside and outside holding parts 20 and 18 on the lower support part 82.

Also, by providing the outside holding part 18 and the inside holding part 20 on the opening member 12, and positioning the lower support part 82 therebetween, it is possible to skillfully use the internal space of the opening member 12. Therefore, while suppressing the distance A from the annular joining part 72 to the axial direction outside end of the outside holding part 18 which is difficult to extend, it is possible to make the projecting dimension B of the lower support part 82 downward in the axial direction larger, so as to increase the bearing capacity of the elastic valve body 16 by the opening member 12. In particular, since the aforementioned distance A is kept small, it is possible to avoid a decrease in insertion and removal operability of the male connector or an increase in size of the medical valve 10.

Furthermore, with this embodiment, the flange part 85 broadening to the outer peripheral side is provided at the projecting tip part of the lower support part 82, and by the flange part 85 being compressed and sandwiched between the outside holding part 18 and the inside holding part 20 in the axial direction, falling out of the elastic valve body 16 from the medical valve 10 is even more effectively prevented. In particular, the lower support part 82 extends further downward in the axial direction than the annular shoulder part 50 of the outside holding part 18, and the space provided for the flange part 85 can also be efficiently ensured.

Yet further, with this embodiment, the locking convex part 60 is provided so as to project downward from the inner surface of the outside holding part 18, and the locking recess 86 is provided on the top surface of the flange part 85 at a position corresponding to the locking convex part 60. By these locking convex part 60 and the locking recess 86 being fit and locked, it is possible to even more effectively prevent the elastic valve body 16 from falling out from the medical valve 10.

In particular with this embodiment, the thin wall part 66 is provided at the axial direction middle part of the inside holding part 20, and the thickness becomes gradually larger therefrom toward inside in the axial direction. Thus, the thickness of the axial direction middle part of the inside holding part 20, for which the elastic valve body 16 that is elastically deformed during insertion of the syringe 88 is pressed against its inner peripheral surface, is made relatively small. In addition, with the inside holding part 20, by making the thickness smaller, considering the material setting, or the like, the deformation rigidity at least at the axial direction middle part is smaller than that of the male connector part of the syringe 88 and the small diameter tube part 48 of the outside holding part 18.

By so doing, when the elastic valve body 16 elastically deformed in accordance with insertion of the syringe 88 is pressed on the inner peripheral surface of the inside holding part 20, this pressing force can be efficiently transmitted as a pressing force on the lower support part 82 of the elastic valve body 16 arranged tightly on the outer peripheral side of the inside holding part 20. In particular, with this embodiment, the axial direction dimension B of the lower support part 82 is made greater than the radius E of the center part 68 of the elastic valve body 16, so that it is possible to apply the pressing force to the lower support part 82 across the entire surface of the center part 68. Also, since the rigidity of the outside holding part 18 is high, the lower support part 82 is sandwiched even more strongly between the inside holding part 20 and the outside holding part 18 so as to be held with a high bearing capacity. In addition, the angle change part 83 is provided at the inner peripheral surface at the axial direction middle part of the lower support part 82. In particular, by the angle change part 83 having a concave round surface, the thin part 84 is formed at the lower support part 82. In combination with the lower support part 82 being gradually thicker inward in the axial direction than the thin part 84, pulling out of the lower support part 82 is more strongly inhibited, and falling out of the elastic valve body 16 is more effectively prevented.

Also, in the initial attached state, the lower support part 82 is attached in a state not compressed between the inside holding part 20 and the outside holding part 18 in the radial direction. By so doing, deformation or absorption is allowed in relation to external force or the like that occurs when an object bumps the outer peripheral surface of the housing, reducing the damage rate of the outside holding part 18, the inside holding part 20 or the like constituting the housing. Also, even in a case when the elastic valve body 16 that is elastically deformed with insertion of the syringe 88 is pressed on the inner peripheral surface of the inside holding part 20, this pressing force is transmitted with a reduction by compression of the lower support part 82. As a result, it is possible to avoid having excessive external force applied to the outside holding part 18, and damage of the outside holding part 18 is effectively prevented.

With the medical valve 10 of this embodiment, the outside holding part 18, the inside holding part 20, and the valve housing main body 22 are respectively separate members. Also, the mode wherein the inside holding part 20 is supported between the outside holding part 18 and the valve housing main body 22 can be realized by ultrasonic welding of the outside holding part 18 and the valve housing main body 22.

Also, with this embodiment, at the lower support part 82, since the diameter dimension of the projecting direction tip side is greater than that of the projecting direction base end side, it is possible to ensure a large capacity of the fluid flow path 90 inside of the medical valve 10. By so doing, during insertion of the syringe 88, the elastic deformation area of the elastic valve body 16 is stably ensured, and it is easily possible to insert the syringe 88 in the medical valve 10.

Furthermore, the outside holding part 18 and the inside holding part 20 have a tube shape that broadens inward in the axial direction, and are shaped so that the radial direction distance between the opposite surfaces of the inside and outside holding parts 20 and 18 becomes larger inward in the axial direction. In specific terms, the outside holding part 18 has its thickness dimension gradually become larger inward in the axial direction, and the inclination angle of the inner peripheral surface of the lower support part 82 and the inner peripheral surface at the axial direction middle part of the inside holding part 20 is greater than that of the inner peripheral surface of the small diameter tube part 48 of the outside holding part 18, so that the thickness dimension becomes gradually larger inward in the axial direction for the lower support part 82 and the inside holding part 20 as well. By so doing, the support of the outside and inside holding parts 18 and 20 and the elastic valve body 16 by the valve housing main body 22 can be realized with even more stability.

Above, we gave a detailed description of the embodiment of the present invention, but the present invention is not limited by those specific descriptions, and can be implemented in modes with various modifications, revisions, improvements and the like added based on the knowledge of a person skilled in the art, and those kinds of mode of embodiment are also included in the scope of the present invention as long as they do not stray from the gist of the present invention.

Figure 12:
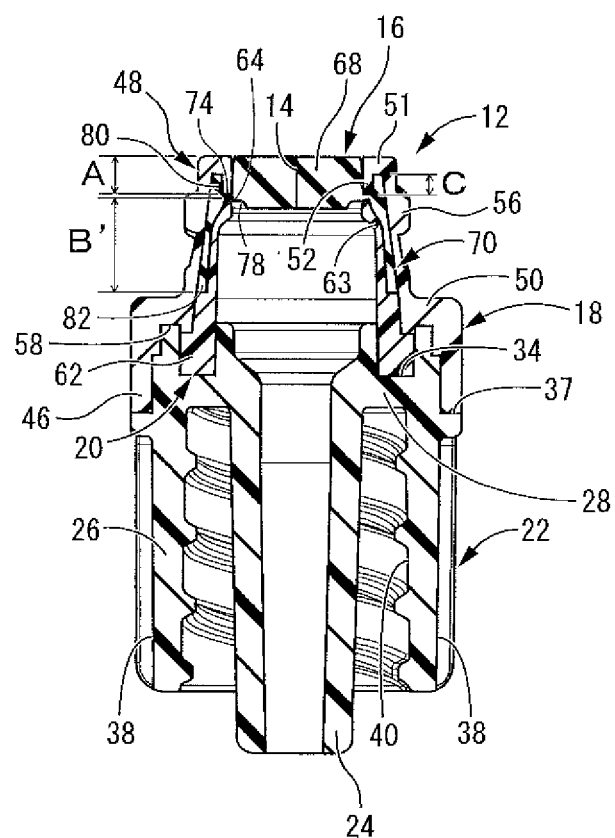
FIG. 12 is a vertical cross section view showing another mode of the medical valve of the present invention, corresponding to FIG. 5.

For example, with the embodiment noted above, the lower support part 82 of the tubular support part 70 extends further inward in the axial direction than the annular shoulder part 50 of the outside holding part 18, and the flange part 85 and locking recess 86 or the like are formed on its tip, but the invention is not limited to this mode. Specifically, as shown in FIG. 12, for example it is also possible to suitably use a mode with which in the attached state, the lower end surface of the lower support part 82 is positioned above the annular shoulder part 50, and the axial direction dimension B' from the lower surface of the annular joining part 72 to the axial direction inside end of the lower support part 82 is made larger than the axial direction dimension A from the top surface of the annular joining part 72 to the axial direction outside end of the outside holding part 18 or the axial direction dimension C from the top surface of the annular joining part 72 to the tip end surface of the upper support part 80 (A<B' or C<B'). With this mode, the radial direction distance between the opposite surfaces of the inside and outside holding parts 20 and 18 is slightly smaller than the radial direction thickness dimension of the lower support part 82 of the elastic valve body 16 before attaching, so that the lower support part 82 is compressed by the inside and outside holding parts 20 and 18. Also, as is clear from FIG. 12 as well, the flange part 85, the locking convex part 60 and the locking recess 86 and the like are not essential. With the medical valve having this constitution, it is possible to make the friction between the lower support part 82 and the inside/outside holding parts 20, 18 greater, thereby sufficiently exhibiting the fall-out prevention effect of the elastic valve body 16. Of course, the size of the axial direction dimension B from the lower surface of the annular joining part 72 to the axial direction inside end of the lower support part 82 is not limited in any way as long as it extends further downward than the annular joining part 72 in the attached state of the elastic valve body 16 to the opening member 12.

Also, with the embodiment noted above, the inside holding part 20 and the valve housing main body 22 were separate parts, but they can also be integrally formed.

Furthermore, with the embodiment noted above, the locking convex part 60 was formed projecting downward at the lower opening end edge part of the small diameter tube part 48 of the outside holding part 18, but the invention is not limited to this mode. Specifically, the locking convex part 60 can be formed on the outside holding groove 54 or the axial direction middle part of the outside holding part 18, or can also be formed projecting upward from the inside holding part 20.

Also, when providing the radial direction projecting part at the axial direction inside end part of the lower support part 82 of the elastic valve body 16, instead of or in addition to the flange part 85 extending outward in the radial direction as with the embodiment noted above, it is also possible to use a radial direction projecting part extending inward in the radial direction, and to engage it in the axial direction with the opening member 12 such as the inside holding part 20 or the like, or to hold it compressively in the axial direction.

With the embodiment noted above, the inside and outside engaging claws 64 and 52 and the inner and outer annular grooves 76 and 74 were formed annularly across the entire periphery in the circumference direction, but for example it is also possible to have the inner and outer engaging claws formed intermittently in the circumference direction, or to change the height of the engaging claws on the circumference in a stepwise or continuous manner. Also, the inner and outer annular grooves can also be formed intermittently by corresponding with the position and size of the inner and outer engaging claws or the like. Since the upper support part of the elastic valve body can more easily separate from the housing (opening member) than the lower support part, it is preferable that the elastic valve body have at least an outer annular groove. Of course, the outer annular groove and the inner annular groove are not essential for the present invention, and it is acceptable as long as there is a slim part supported by the inner and outer holding parts. Also, it is preferable that the outside engaging claw provided on the outside holding part be engaged with the outer annular groove.

Furthermore, with the tubular support part of the medical valve, the thin part provided at the part projecting inward in the axial direction or the radial direction projecting part provided at the tip of the part projecting inward in the axial direction or the like do not have to be formed continuously across the entire periphery in the circumference direction, and can also be provided partially on the circumference. Also, with the tubular support part, the radial direction projecting part does not have to be provided at the tip of the projecting part that projects inward in the axial direction, and can also be provided at the axial direction middle part of that projecting part, for example.

KEYS TO SYMBOLS

10: Medical valve, 12: Opening member, 14: Slit, 16: Elastic valve body, 18: Outside holding part, 20: Inside holding part, 22: Valve housing main body (opening member main body), 35: Supporting wall, 36: Projecting part for welding, 50: Annular shoulder part, 52: Outside engaging claw, 60: Locking convex part, 64: Inside engaging claw, 65: Expanding inclined surface, 66: Thin wall part, 68: Center part, 70: Tubular support part, 72: Annular joining part, 74: Outer annular groove, 76: Inner annular groove, 80: Upper support part, 82: Lower support part, 83: Angle change part, 84: Thin part, 85: Flange part (radial direction projecting part), 86: Locking recess, 87: Locking projection, 88: Syringe (male connector), 90: Fluid flow path

The invention claimed is:

1. A medical valve comprising:
an opening member constituting an opening part of a fluid flow path; and
a disk-shaped elastic valve body having a slit formed on a center part thereof and being mounted on the opening member, the disk-shaped elastic valve body being configured to enable a male connector to be repeatedly inserted and removed through the slit, wherein:
the disk-shaped elastic valve body includes
a slim part that is located at and projected in a radial direction perpendicular to an axial direction from an outer peripheral side of the center part and whose axial direction dimension is thinner than the center part, with a bottom of the center part being lower than a bottom of the slim part in the axial direction, and
a tubular support part that is formed further to the outer peripheral side than the slim part and projects inward further than the center part in the axial direction,
the opening member includes
a tube-shaped outside holding part overlapping an outer peripheral surface of the tubular support part, and
a tube-shaped inside holding part overlapping an inner peripheral surface of the tubular support part,
the slim part of the disk-shaped elastic valve body is sandwiched and supported between the tube-shaped inside holding part and the tube-shaped outside holding part in the axial direction,
a part of the tubular support part, which projects inward in the axial direction, is sandwiched and supported between the tube-shaped inside holding part and the tube-shaped outside holding part in the radial direction, and an axial direction dimension of the part of the tubular support part is larger than a radius of the center part of the disk-shaped elastic valve body which is a region that extends inward in the radial direction from an inner peripheral portion of the slim part.

2. The medical valve according to claim 1, wherein the tubular support part includes a radial direction projecting part being integrally formed at a tip side of the part of the tubular support part and extending in the radial direction, and the radial direction projecting part is engaged with the opening member.

3. The medical valve according to claim 2, wherein the radial direction projecting part extends outward in the radial direction from the tubular support part, and the slim part and the radial direction projecting part of the disk-shaped elastic valve body are compressed in the axial direction in an attached state to the opening member.

4. The medical valve according to claim 2, wherein a locking projection projecting outward in the axial direction is formed on the radial direction projecting part, and the locking projection is locked to the opening member.

5. The medical valve according to claim 1, wherein the tubular support part includes a thin part and a thick part provided in the part of the tubular support part, and the thick part is positioned further inward in the axial direction than the thin part.

6. The medical valve according to claim 1, wherein the tube-shaped inside holding part is configured to be pressed to a side of the tubular support part on an outer periphery thereof by the disk-shaped elastic valve body that elastically deforms in accordance with insertion of the male connector into the slit.

7. The medical valve according to claim 6, wherein a rigidity of the tube-shaped inside holding part is smaller than rigidities of the tube-shaped outside holding part and the male connector.

8. The medical valve according to claim 1, wherein the disk-shaped elastic valve body includes inner and outer annular grooves that extend in a circumference direction respectively on both inner and outer surfaces in the axial direction at the outer peripheral side of the center part, and the slim part is constituted between bottom parts of the inner and outer annular grooves, the tube-shaped outside holding part includes an outside engaging claw that enters the outer annular groove on the outer surface of the disk-shaped elastic valve body while the tube-shaped inside holding part includes an inside engaging claw that enters the inner annular groove on the inner surface of the disk-shaped elastic valve body, and an inner surface of a base end side of the inside engaging claw of the tube-shaped inside holding part inclines and expands inward in the axial direction so as to define an expanding inclined surface.

9. The medical valve according to claim 1, wherein the tube-shaped outside holding part has a wall thickness that becomes gradually larger as it goes inward in the axial direction at least at an axial direction middle part for which a screw thread is not provided on an outer peripheral surface thereof, and the tube-shaped outside holding part gradually inclines outward in the radial direction as it goes inward in the axial direction, and each of an inner peripheral surface of the part of the tubular support part and an inner peripheral surface of the tube-shaped inside holding part inclines at a sharper angle than an inner peripheral surface of the tube-shaped outside holding part and broadens inward in the axial direction, at least at a part further inward than a middle part in the axial direction.

10. The medical valve according to claim 1, wherein the axial direction dimension of the part of the tubular support part that is sandwiched between the tube-shaped inside holding part and the tube-shaped outside holding part in the radial direction, is greater than twice an axial direction dimension of the center part.

11. The medical valve according to claim 1, wherein the tubular support part that is formed further to the outer peripheral side than the slim part projects further outward than the slim part in the axial direction.

12. The medical valve according to claim 1, wherein a top part of the tube-shaped outside holding part is a circular tip wall part that broadens in a bent state, and at an inner periphery edge part of the circular tip wall part, an outside engaging claw is formed extending downward so as to be folded back inward in the axial direction, and an upper surface of the slim part abuts the outside engaging claw.

13. The medical valve according to claim 1, wherein the part of the tubular support part includes a thin part and a thick part, the thin part is positioned further inward in the axial direction than the slim part, and the thick part is positioned further inward in the axial direction than the thin part.

14. The medical valve according to claim 1, wherein the axial direction dimension of the part of the tubular support part is larger than half an axial direction dimension of the tubular support part.

15. A medical valve comprising:

an opening member constituting an opening part of a fluid flow path; and a disk-shaped elastic valve body having a slit formed on a center part thereof and being mounted on the opening member, the disk-shaped elastic valve body being configured to enable a male connector to be repeatedly inserted and removed through the slit, wherein:

the disk-shaped elastic valve body includes
 a slim part that is located at and projected in a radial direction perpendicular to an axial direction from an outer peripheral side of the center part and whose axial direction dimension is thinner than the center part, with a bottom of the center part being lower than a bottom of the slim part in the axial direction, and
 a tubular support part that is formed further to the outer peripheral side than the slim part and projects inward further than the center part in the axial direction, the opening member includes
 a tube-shaped outside holding part overlapping an outer peripheral surface of the tubular support part, and
 a tube-shaped inside holding part overlapping an inner peripheral surface of the tubular support part, the slim part of the disk-shaped elastic valve body is sandwiched and supported between the tube-shaped inside holding part and the tube-shaped outside holding part in the axial direction, a part of the tubular support part, which projects inward in the axial direction, is held in a compressed state between the tube-shaped inside holding part and the tube-shaped outside holding part in the radial direction, and an axial direction dimension of the part of the tubular support part is larger than a radius of the center part of the disk-shaped elastic valve body which is a region that extends inward in the radial direction from an inner peripheral portion of the slim part.

16. The medical valve according to claim 15, wherein the axial direction dimension of the part of the tubular support part is larger than half an axial direction dimension of the tubular support part.

17. A medical valve comprising:
an opening member constituting an opening part of a fluid flow path; and
a disk-shaped elastic valve body having a slit formed on a center part thereof and being mounted on the opening member, the disk-shaped elastic valve body being configured to enable a male connector to be repeatedly inserted and removed through the slit, wherein:
the disk-shaped elastic valve body includes
inner and outer annular grooves that extend in a circumference direction respectively on both inner and outer surfaces of an outer periphery part of the disk-shaped elastic valve body,
a slim part positioned between bottom parts of the inner and outer annular grooves, the slim part having an axial direction dimension thinner than the center part, with a bottom of the center part being lower than a bottom of the slim part in the axial direction, and
a tubular support part that is formed at an outer peripheral side of the slim part and projects inward further than the center part and outward further than the slim part in the axial direction,
the opening member includes
a tube-shaped outside holding part overlapping an outer peripheral surface of the tubular support part, and
a tube-shaped inside holding part overlapping an inner peripheral surface of the tubular support part,
the tube-shaped outside holding part and the tube-shaped inside holding part are engaged with the respective annular grooves on the outer surface and the inner surface of the disk-shaped elastic valve body,
a part of the tubular support part, which projects inward in the axial direction, is sandwiched and supported between the tube-shaped inside holding part and the tube-shaped outside holding part in a radial direction perpendicular to the axial direction,
an axial direction dimension of the part of the tubular support part is larger than a radius of the center part of the disk-shaped elastic valve body which is a region that extends inward in the radial direction from an inner peripheral portion of the slim part, and
the axial direction dimension of the part of the tubular support part is larger is larger than an axial direction dimension of the center part of the disk-shaped elastic valve body.

18. The medical valve according to claim 17, wherein the axial direction dimension of the part of the tubular support part is larger than half an axial direction dimension of the tubular support part.

\* \* \* \* \*